US008663160B2

(12) United States Patent
Sternberg et al.

(10) Patent No.: US 8,663,160 B2
(45) Date of Patent: Mar. 4, 2014

(54) DEVICE TO INDICATE PRIMING OF AN INFUSION LINE

(71) Applicants: Baxter International Inc., Deerfield, IL (US); Baxter Healthcare S.A., Glattpark (CH)

(72) Inventors: Shmuel Sternberg, Palatine, IL (US); Siddharth B. Desai, Ladera Ranch, CA (US); Larry Black, Costa Mesa, CA (US); Robin G. Pauley, Lake Villa, IL (US)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 0 days.

(21) Appl. No.: 13/741,843

(22) Filed: Jan. 15, 2013

(65) Prior Publication Data

US 2013/0125808 A1     May 23, 2013

Related U.S. Application Data

(63) Continuation of application No. 12/555,606, filed on Sep. 8, 2009, now Pat. No. 8,398,590.

(60) Provisional application No. 61/095,339, filed on Sep. 9, 2008.

(51) Int. Cl.
    *A61M 5/00*     (2006.01)
(52) U.S. Cl.
    USPC ........................... 604/111; 604/126; 604/404
(58) Field of Classification Search
    CPC ...................................................... A61M 5/00
    USPC .................. 340/603, 604; 604/111, 120–127, 604/404–406
    See application file for complete search history.

(56) References Cited

U.S. PATENT DOCUMENTS

| 3,303,846 A | 2/1967 | Ogle |
| 3,659,749 A | 5/1972 | Schwartz |
| 3,678,931 A | 7/1972 | Cohen |
| 3,682,174 A | 8/1972 | Cohen |
| 3,685,514 A | 8/1972 | Cheney |

(Continued)

FOREIGN PATENT DOCUMENTS

| GB | 2032401 | 5/1980 |
| WO | WO 2007/134066 | 11/2007 |
| WO | WO 2008/011581 | 1/2008 |
| WO | WO 2009/030056 | 3/2009 |

*Primary Examiner* — Nicholas Lucchesi
*Assistant Examiner* — Gerald Landry, II
(74) *Attorney, Agent, or Firm* — Greer, Burns & Crain, Ltd.; Jeffrey C. Nichols

(57) ABSTRACT

A priming indicator for a fluid infusion system includes a luer cap or other component of the infusion system having an indicator surface covered by a membrane. The membrane exhibits a first visual characteristic, such as being opaque, when dry and exhibits a second characteristic, such as becoming less opaque, when wet. Once the membrane becomes wet, indicia on the surface, which may be provided on a rod at least partially covered by the membrane, becomes visible, thereby indicating an intravenous tube to which the luer cap is secured has been primed or is nearly primed. The indicator may alternately be employed at an upstream end of an infusion set, such as at the port of a medical bag providing a supply of fluid, to indicate a low level of fluid in the medical bag.

17 Claims, 12 Drawing Sheets

(56) References Cited

U.S. PATENT DOCUMENTS

| | | |
|---|---|---|
| 4,405,317 A | 9/1983 | Case |
| 4,581,016 A | 4/1986 | Gettig |
| 4,929,230 A | 5/1990 | Pfleger |
| 5,067,948 A | 11/1991 | Haber et al. |
| 5,318,520 A | 6/1994 | Nakao |
| 5,779,668 A | 7/1998 | Grabenkort |
| 5,785,682 A | 7/1998 | Grabenkort |
| 5,876,372 A | 3/1999 | Grabenkort et al. |
| 5,897,530 A | 4/1999 | Jackson |
| 2001/0021820 A1 | 9/2001 | Lynn |
| 2005/0132826 A1 | 6/2005 | Teugels |
| 2005/0267413 A1 | 12/2005 | Wang et al. |
| 2007/0106243 A1* | 5/2007 | Faries et al. .......... 604/404 |
| 2007/0293822 A1* | 12/2007 | Crawford et al. ......... 604/175 |
| 2008/0021392 A1* | 1/2008 | Lurvey et al. .......... 604/111 |
| 2008/0205481 A1* | 8/2008 | Faries et al. .......... 374/138 |

* cited by examiner

DEVICE TO INDICATE PRIMING OF AN INFUSION LINE

REFERENCE TO RELATED APPLICATIONS

This is a Continuation of, and claims 35 USC 120 priority from U.S. application Ser. No. 12/555,606 filed Sep. 8, 2009, which is a non-provisional application entitled to the benefit of the filing date of U.S. Provisional Application No. 61/095,339, filed Sep. 9, 2008, as to all subject matter commonly disclosed therein.

FIELD OF THE DISCLOSURE

This disclosure relates generally to a priming indicator for a medical fluid infusion system, and more specifically, to a component of the infusion system that serves as a priming indicator to indicate when an infusion system is primed.

BACKGROUND

Many medical patients require precise intravenous delivery of a fluid in desired rates such as either continuous delivery or delivery having a particular flow rate profile. Continuous delivery may be accomplished using gravity or pumps. Conventional medical pumps can also provide controlled drug infusion wherein a drug may be administered at a more precise rate than gravity administration that maintains the drug concentration within a therapeutic margin and out of an unnecessary or possibly toxic range.

Medical pumps may facilitate administration of intravenous therapy to patients both in and outside of a clinical setting. Outside a clinical setting, doctors have found that in many instances patients can return to substantially normal lives, provided that they receive periodic or continuous intravenous administration of medication through the use of ambulatory pumps. Among the types of therapies requiring this kind of administration are antibiotic therapy, chemotherapy, pain control therapy, nutritional therapy, and several other types known by those skilled in the art. In many cases, patients receive multiple daily therapies.

Certain medical conditions require low rate infusions of drugs in solution over relatively long periods, such as from two hours to multiple days. These conditions and others have combined to promote the development of increasingly lightweight, portable or ambulatory infusion pumps that can be worn by a patient and are capable of administering a continuous supply of medication at a desired rate, or provide several doses of medication at scheduled intervals.

A medical fluid infusion system of the types described above typically provides a fluid flow path (or tubing line) between a medical fluid source and a patient. A flow restrictor may be employed along the length of such flow path to limit or control fluid flow to the patient in accordance with a desired fluid therapy or protocol. These systems usually are supplied in a sterile, non-filled condition and the pharmacist or other healthcare provider then compounds or injects the desired medication into the medical fluid source. Sterility of the flow path is maintained until use typically by the use of a luer cap. Prior to connection of the flow path to the patient this flow path must be primed to remove any air bubbles. To allow the air to escape the priming typically is done by removal of the luer cap and visually observing the fluid flow through the flow path until a small amount is emitted from a luer connection at the end of the flow path. Then the luer connection is attached to a catheter which has been inserted into the patient.

This process, however, is often time consuming and requires the constant attention of medical personnel to determine whether priming has been accomplished by watching the end of the tubing line to see if the fluid is dripping at the end of the line. The slower the flow rate of fluid through the flow line the longer the medical personnel will need to observe the filling of the flow line.

Because the fluid may be costly or may be harmful if exposed to persons, it is important to know as soon as possible once an intravenous line has been fully primed and is ready to have its contents delivered into a patient without exposing the environment to the fluid. It is also important that the priming can occur without the necessity of constant monitoring.

U.S. Pat. No. 5,318,520 to Nakao describes a device for use in intravenous feeding, having a reservoir of an intravenous fluid and an intravenous tube connected at one end to a reservoir. The tube is provided on an inner surface with a layer of a water-soluble biocompatible material that is visible through a transparent wall of the tube. During use, an intravenous fluid is flushed through the tube until the water-soluble biocompatible layer dissolves and is no longer visible. This is accomplished using an indicator layer with a predetermined thickness and density, whereby the layer dissolves upon flushing of a predetermined amount of fluid through the tube. Effectively, this provides an indication to a nurse or doctor that an intravenous line may or may not have been sufficiently flushed with intravenous fluid to remove all of the residual air from the line. Nakao, U.S. Pat. No. 5,318,520, also describes an alternate embodiment in which a separate connector piece is provided on a free end of the intravenous tube, with the inner surface of only the separate connector piece being provided with an inner surface having the layer of water-soluble biocompatible material that dissolves upon flushing of the tube and connector member with intravenous fluid. In each embodiment, after priming, any residual biocompatible material on the interior of the tube or connector gets flushed into the patient with the intravenous fluid.

Accordingly, it is realized that there are still unmet needs for a priming indicator in infusion systems that provides an indication to medical personnel when priming of the flow path is complete, and without adding any leachables or potential contaminants to intravenous fluid to be delivered to a patient.

SUMMARY

A component of the present disclosure includes a housing with a cavity that holds a colored member surrounded by an opaque membrane. When the membrane becomes wet with fluid in an infusion line to which the luer cap is connected, the membrane loses its opacity, thereby turning at least partially transparent and revealing the colored member, thus indicating that contact of that component with the fluid flowing through the infusion line. When the component is placed at the end of the infusion line this contact may represent that the priming of the infusion line is complete. Fluid is prevented from flowing through an end of the component by a hydrophobic vent, which allows air to be properly expelled from the line while maintaining the liquid in the line.

In one embodiment of the present disclosure, the component includes a luer cap to indicate priming of an infusion line, and includes a member inserted into a cavity of a housing of the luer cap and a membrane covering or surrounding at least a portion of the member. The membrane is opaque while dry, concealing the member from view, and transparent when wet, revealing the surrounded portion of the member.

In another embodiment of the present disclosure, there is a device for administering fluid, including a reservoir of an intravenous fluid, a tubing line connected at one end of the reservoir and providing the intravenous fluid to flow therethrough, and a luer connected to the tubing line downstream of the reservoir and configured to receive a luer cap, wherein the luer cap indicates when the fluid from the reservoir has flowed therein. The luer cap indicates that the fluid has flowed therein by giving a visual change such as changing color.

In still another embodiment of the present disclosure, there is a method for administering fluid, including providing a reservoir of an intravenous fluid; providing a tubing line connected at one end of the reservoir and providing the intravenous fluid to flow therethrough; and providing a luer connected to the tubing line downstream of the reservoir and configured to received a luer cap, wherein the luer cap indicates when the fluid from the reservoir has flowed therein. The luer cap indicates that the fluid has flowed therein by changing from opaque to transparent, revealing an otherwise-concealed colored member, or a member that is provided with some other visually discernable indicia to indicate priming is complete.

According to one aspect of the present disclosure, the luer cap includes a hydrophobic vent to allow air to flow out of the luer cap while preventing fluid from flowing therethrough.

In still another aspect of the present disclosure, the membrane is a microporous structure comprised of strands that turn transparent when fluid having a refractive index that matches or substantially matches the refractive index of the strands.

In yet another aspect of the present disclosure, a membrane that provides visual indicia or alternate detection of the priming of an infusion system is located along an administration tube, upstream of a luer cap.

In an additional aspect of the present disclosure, the membrane may provide visual indicia or alternate means for detection of an absence of fluid flowing through a given component of an infusion system.

The visual indicia of the membrane of the various embodiments of the present disclosure may include, by way of example only, a change in transparency or opacity, a change in color, or a change in appearance (or absence of appearance) of an image, such as a word, a letter, or an icon on the membrane.

The membrane may provide additional or alternate means for detection of the presence, or absence, of fluid flow through a given component of an infusion system, such as a sensing system that communicates a signal to a controller in operable communication with a device that emits at least one of an audible or a visual alarm that alerts a medical professional to a change in status of flow through the given component. The alarm may include a pre-recorded audible message, a text message, e-mail, or a vibration of a pager device worn by the medical professional. The alarm may be distinct for different individual patients, such that one or more medical professionals to whom the alarm is directed might know by the characteristics of the alarm which of a plurality of patient's infusion system is fully primed.

Additional features and advantages are described herein, and will be apparent from, the following Detailed Description and the figures.

DETAILED DESCRIPTION

Figure 1:
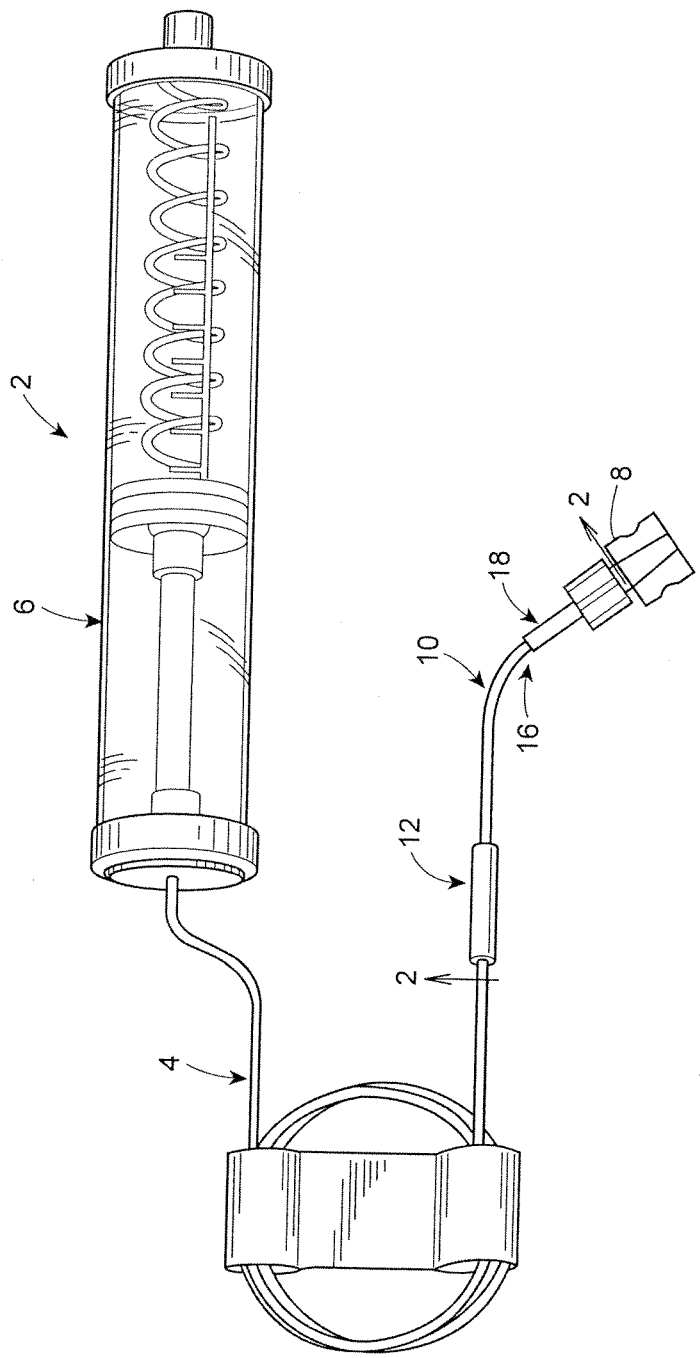
FIG. 1 is a perspective view of a conventional medical fluid administration or infusion set, including a fluid source and an infusion flow path directed for delivering fluid from the source to a patient.

FIG. 1 illustrates a conventional medical fluid delivery or administration system or infusion system, generally at 2. The illustrated fluid delivery system 2 is an ambulatory system for mobile or ambulatory patients. However, this is for exemplary purposes only, and the present invention is not limited to ambulatory fluid delivery systems and may be equally applied to any other medical fluid infusion systems for patients, including patients that are bedfast or otherwise non-ambulatory. In FIG. 1, the system 2 includes tubing 4 which defines a fluid flow path communicating between a fluid source, generally indicated at 6, and the patient (not shown). For attachment to a patient, the illustrated system includes a needle, needle-less cannula or male luer connector generally indicated at 8, although any other patient access device such as a needle or catheter may also be employed.

The fluid source 6 may be any suitable source of medical fluid such as medicament, intravenous solution, or combination. The fluid source may include an infuser pump, such as an expandable bladder type pump, which increases in volume and pressure as fluid is introduced therein and subsequently contracts to force fluid out of the bladder during fluid delivery. Alternatively, the fluid source 6 may be a fluid container that provides fluid flow due to gravity such as, for example, by locating the fluid source at a height above the entry site to the patient, where the pressure head from the column of fluid above the entry site is sufficient to provide fluid flow to the patient. Other fluid sources and means of propelling the fluid may also be employed and are not limited to the above described systems.

The illustrated ambulatory fluid delivery system in FIG. 1 includes a flow restrictor, generally indicated at 10, which limits or controls fluid flow for preventing a desired rate of fluid flow to the patient. The flow restrictor may take any of different suitable forms. As illustrated, the flow restrictor 10 defines a length of tubing extending between a connector, generally indicated at 12, at the upstream end 14 of the flow restrictor 10 and an adaptor, generally indicated at 18, such as a male luer at the downstream end 16 of the flow restrictor, which may connect to the patient access device 8. There may also be an additional length of tubing between the flow restrictor 10 and the adaptor 18.

Figure 2:
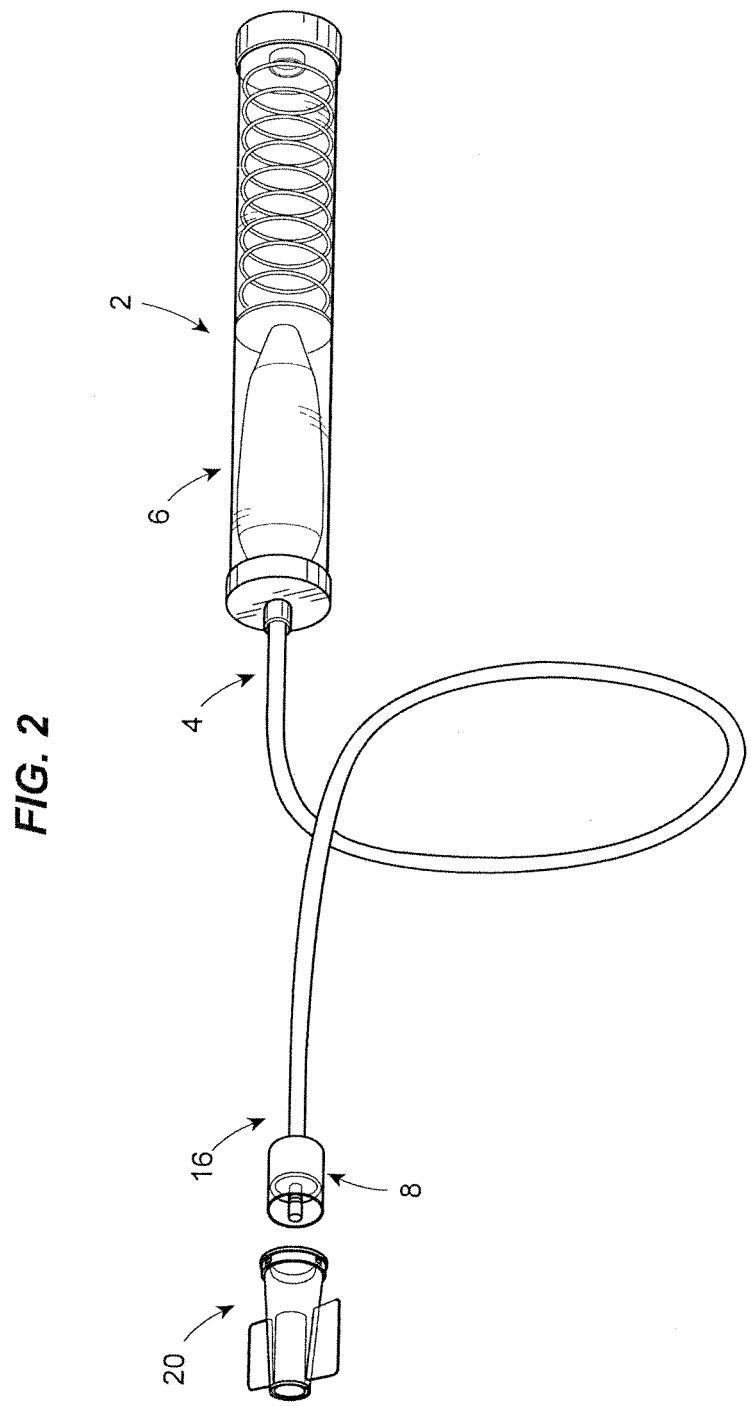
FIG. 2 is a perspective view of a medical fluid administration or infusion set, similar to that depicted in FIG. 1, with an exploded view of a luer with a luer cap according to the present disclosure.

FIG. 2 is a perspective view of an exemplary medical fluid administration or infusion set, similar to that depicted in FIG. 1, with an exploded view of the attached luer with a luer cap of the present disclosure. According to this exemplary embodiment, a male luer 8 is attached at the downstream end 16 of the tubing 4. The luer 8 is provided with a female luer cap 20 that seals fluid within the tubing 4 until it is desired to connect the tubing to the patient. In an embodiment the luer cap 20 prevents the flow of fluid to the patient until the connection to the patient may be performed by an operator (e.g. medical personnel, such as a nurse or doctor). A hydrophobic membrane 26 (FIG. 4) covers a portion of the end of the cap 20 and provides a vent to allow the escape of air or other gas within the tubing 4 during priming of the tubing. The luer cap 20 is provided with a priming indicator that is capable of providing a visual indication to medical personnel when the tubing 4 is fully primed.

The priming indicator may take various forms, such as the form of a membrane 24 that changes its physical appearance upon at least one of the presence or absence of fluid contact with the membrane. In another form, a membrane 24 may change its degree of transparency upon at least one of the presence or absence of fluid contact with the membrane.

Figure 3A:
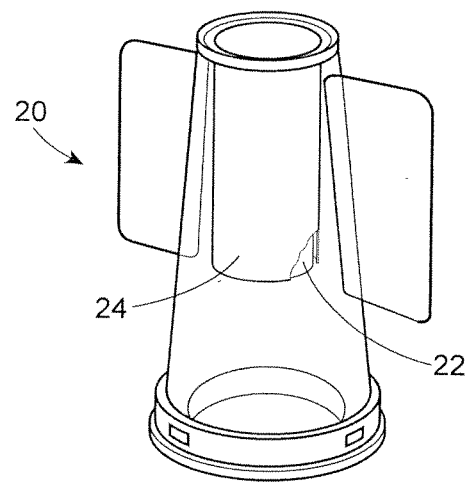
FIG. 3A is an enlarged perspective view of a luer cap according to the present disclosure, partially cut away to reveal a portion of a member such as a rod, which may be colored or provided with other indicia, concealed within an opaque membrane of the luer cap.
Figure 3B:
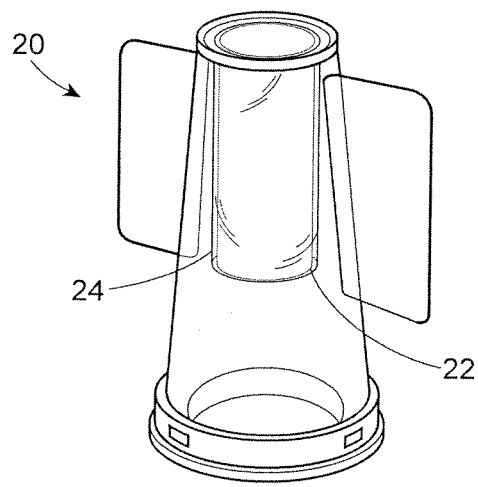
FIG. 3B is an enlarged perspective view of the luer cap depicted in FIG. 3A, after the membrane thereof has been fully wetted, showing that the membrane has changed from opaque to transparent, thereby revealing the rod, so as to provide an indication that the medical fluid administration or infusion set is fully primed.

FIGS. 3A and 3B illustrate a perspective view of a luer cap having a member such as a cylindrical rod, which appears opaque when dry and transparent when wet in accordance with the present disclosure. FIG. 3A illustrates the luer cap 20 prior to fluid flowing into the cap, such that the membrane 24 is opaque. For purposes of clarity in this disclosure, a portion of the opaque membrane 24 is cut away, revealing a portion of a member 22 such as a rod that is colored or provided with other indicia, concealed within an opaque membrane 24 of the luer cap. FIG. 3B, on the other hand, illustrates the luer cap 20 after fluid has flowed into the cap, causing the membrane to become wet and thereby changing its degree of transparency, as described below.

Figure 4:
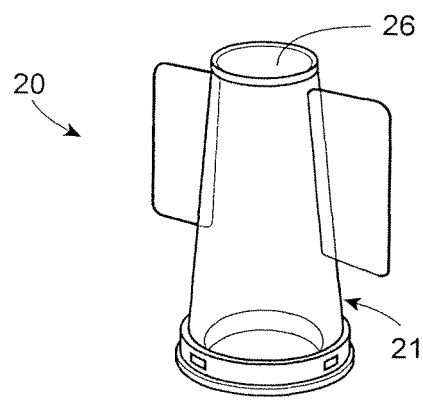
FIG. 4 is an exploded view of the luer cap, membrane and rod of FIGS. 3A and 3B.
Figure 4:
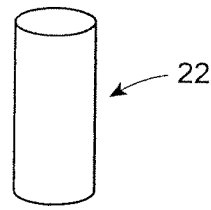
Figure 4:
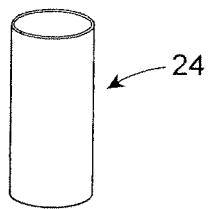

FIG. 4 is an exploded view of the luer cap with a member, which by example only is shown as a cylindrical rod 22, in accordance with the first embodiment of the present disclosure. The luer cap 20 has a housing 21 defining a cavity and an end formed as a vent 26 with an hydrophobic membrane. The member may be preferable formed of a plastic or other material which is inert to contact by the fluid. The cavity is capable of receiving the rod 22, in this embodiment cylindrical in shape, which is coated or covered by a membrane 24. The membrane 24 is made of a material such that when dry, it appears white or opaque, and when wet (for example, when a specified fluid wets the membrane), it loses at least a portion of the opaqueness or changes the degree of transparency, such as becoming almost transparent. The transparency of membrane 24 allows the operator to see the member 22, which has a surface that is visually different from the appearance of the membrane, such as by coloring for visual indication, through the membrane 24 signaling that priming is complete. That is, when the membrane 24 becomes wet with fluid, it becomes at least partially transparent, thereby giving an appearance of the priming indicator changing color.

As an alternative to color, it is recognized that the rod 22 may be provided with some other indicia that becomes visible upon the membrane 24 changing from opaque to transparent upon wetting, such as text (e.g., the word "PRIMED", "WET", or "READY"), or a visual icon such as an image of one or more drops of liquid, which would be desirable to permit use by non-English speakers, accommodate users with limited literacy skills, or reduce the mental processing time for the medical attendant or other user to read and interpret a particular color or word, since an illustration of liquid might more immediately convey to the viewer the fact that the intravenous line is fully primed.

In practice, the membrane 24 is a microporous structure that appears white or opaque to an observer, even when the strands comprising the microporous structure are transparent. It is believed that this result occurs since there is a mismatch between the refractive index of the solid strand and the dry or air filled structure (i.e. membrane). However, if the air is replaced by a fluid with a refractive index somewhat similar to that of the strand, the structure will appear transparent to the observer. In a preferred embodiment, a hydrophilic PTFE, such as Biopore™ made by Millipore Corporation™ is used. This hydrophilic PTFE is a surface modified PTFE membrane that turns transparent when wetted by certain solutions.

Figure 6:
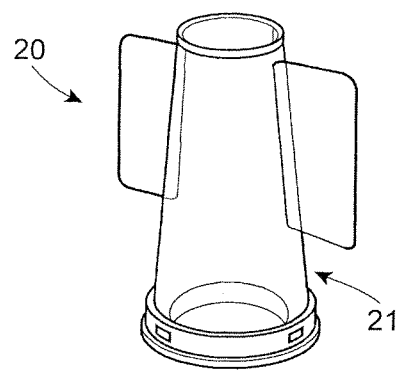
FIG. 6 is an exploded view of the luer cap, membrane and rod of FIGS. 5A and 5B.
Figure 6:
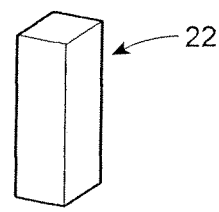
Figure 6:
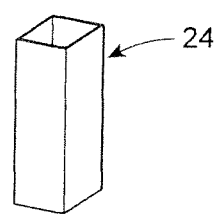
Figure 7B:
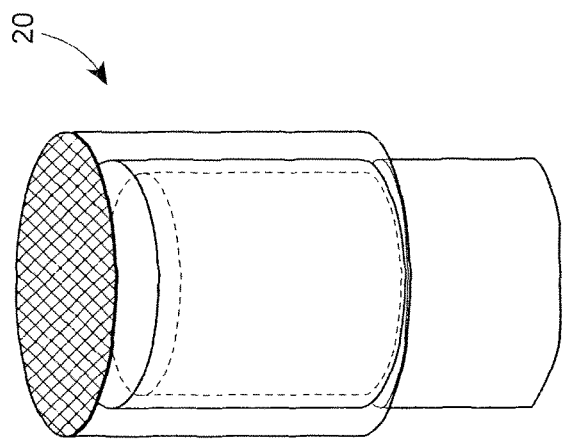
FIG. 7B is a perspective view of the assembled female luer cap having a hydrophobic vent and membrane of FIG. 7A.
Figure 7A:
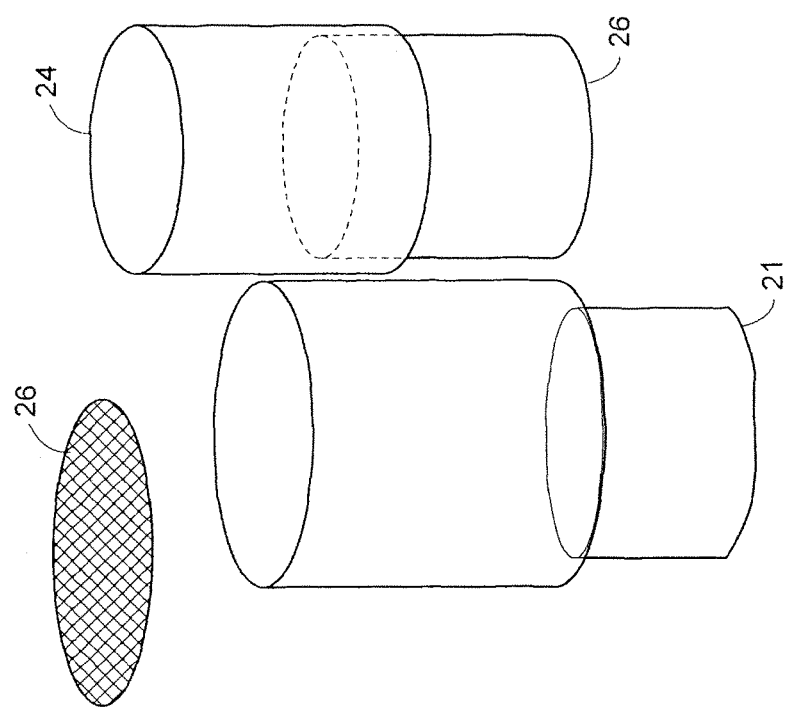
FIG. 7A is an exploded perspective view of a female luer cap having a hydrophobic vent and membrane in accordance with the present disclosure.

FIGS. 7A and 7B show exploded and assembled views of a female luer cap having a hydrophobic vent and membrane in accordance with the present disclosure, similar to FIGS. 4 and 6. As explained above, the luer cap 20 has a housing with a cavity that is capable of receiving a member 22, for example a rod, and membrane 24. More specifically, with reference to FIG. 7, the luer cap 20 is hollow (e.g. has a cavity) which receives the rod 22 which is covered by membrane 24. Once the rod 22 and membrane 24 are inserted into the cavity of luer cap 20, a hydrophobic vent 26 is placed on top. The assembled structure is illustrated on the right-hand portion of the figure, as luer cap 20. As noted, in addition to the rod 22 and membrane 24, the luer cap 20 includes a hydrophobic vent 26. The hydrophobic vent 26 allows air to pass therethrough and escape from the system during priming, but does not allow the passage of the fluid.

Figure 5A:
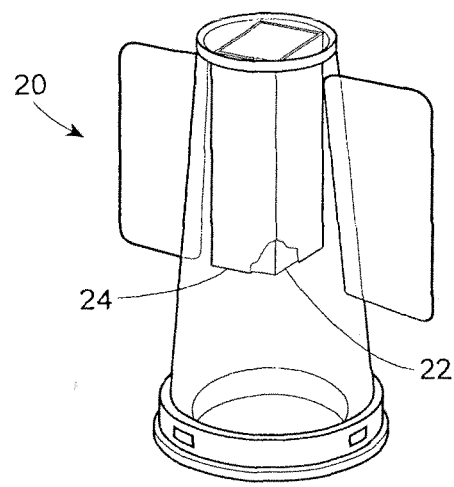
FIG. 5A is an enlarged perspective view, similar to FIG. 3A, of a luer cap according to an alternate embodiment of the present disclosure, showing a membrane and rod of an alternate geometric configuration.
Figure 5B:
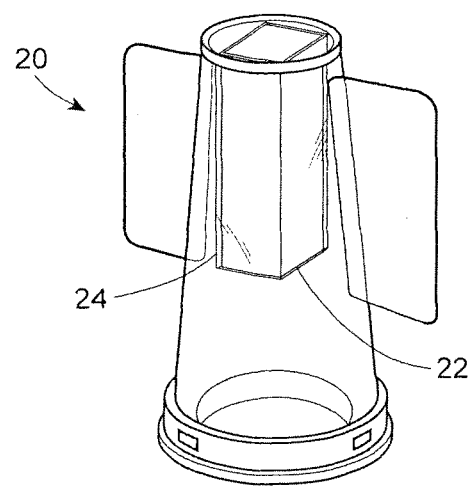
FIG. 5B is an enlarged perspective view of the luer cap depicted in FIG. 5A, after the membrane thereof has been fully wetted, showing that the membrane has changed from opaque to transparent, thereby revealing the rod, so as to provide an indication that the medical fluid administration or infusion set is fully primed.
Figure 8B:
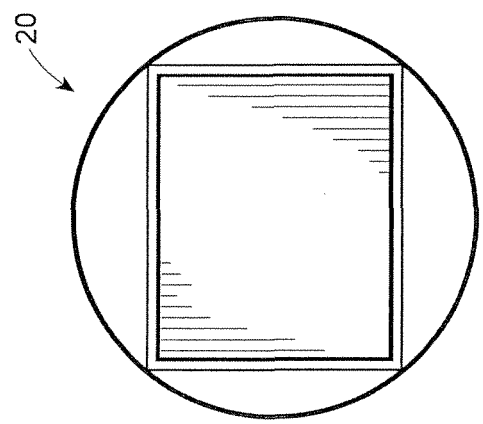
FIG. 8B is a top view of the luer cap similar to that shown in FIGS. 7A and 7B, where the membrane becomes transparent when wet, and a rod within the luer cap is of a rectangular cross-sectional shape.
Figure 8A:
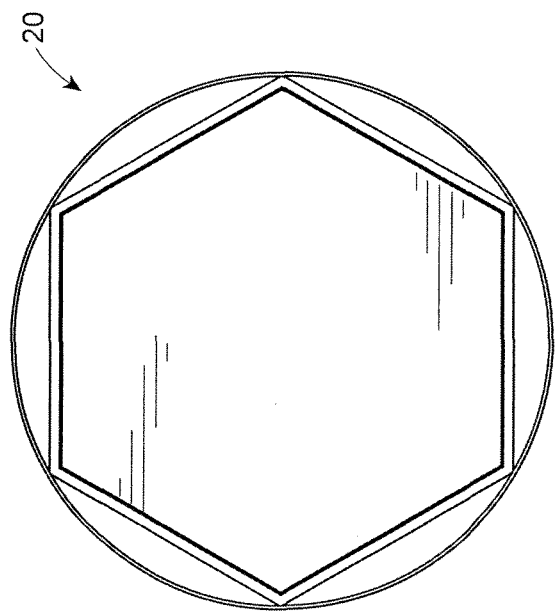
FIG. 8A is a top view of the luer cap similar to that shown in FIGS. 7A and 7B, where the membrane becomes transparent when wet, and a rod within the luer cap is of a hexagonal cross-sectional shape.

FIGS. 5A, 5B and 6 illustrate an alternative embodiment of FIGS. 3A, 3B and 4, respectively. In this embodiment, the member 22 and membrane 24 are of rectangular cross-sectional shape. It should be recognized that the shape of the luer cap and/or the rod are exemplary, and may be shaped in any form as readily understood by the skilled artisan. For example, FIGS. 8A and 8B illustrate atop view of the luer cap with a rod inserted inside the cavity of the housing. In one embodiment, shown in FIG. 8B, the rod is of a rectangular cross-sectional shape. In another embodiment, shown in FIG. 8A, the rod is hexagonal in shape. In yet another embodiment, as shown in FIG. 4, the rod is of a circular cross-sectional shape. The rod may also be hollow.

Referring back to FIG. 2, in use, the assembled luer cap (or priming indicator cap) may be pre-attached to the tubing line 4, or ready to be assembled on the tubing line at any location. At this point, the membrane 24 inside the priming indicator cap is white or opaque since fluid has not flowed through the tube and come into contact with the membrane. Prior to administration of the fluid to the patient, the operator (e.g. medical personnel) of the infusion device begins the priming process to remove air from the tubing line 4. During priming, fluid 6 flows through the tubing line 4 and toward the priming indicator cap. Air within the line is pushed distally by the fluid 6, and escapes from the system through the hydrophobic vent 26 located at the distal end of the priming indicator cap.

When the fluid 6 reaches the capped or distal end of the tubing, it will enter the priming indicator cap and wet the membrane 24. The hydrophobic vent 26 stops fluid from exiting the luer cap. The wetted membrane 24 changes from white/opaque to transparent or semi-transparent, revealing the colored rod, thereby giving an appearance of color change and indicating that priming is complete.

It should be noted that while the rod is preferably plastic, it is not limited to plastic and may be made of any suitable material as understood by the skilled artisan. Also, the use of the term rod does not connote any particular shape such as elongated for other shapes can equally supply a visual indicia upon the membrane coming in contact with a fluid. Moreover, while it is believed the phenomenon of the membrane becoming less opaque is due to the contact with a fluid having a refractive index similar to the material of the membrane, this is not limited to that phenomena.

The visually discernable change in appearance indicates to the operator that the fluid line is primed, and is read for administration of the fluid to a patient. In use, the medical practitioner would wait until the indicia on the surface of the rod 22 becomes visible before removing the luer cap and administering the contents of the intravenous tube to a patient. Or the medical practitioner may begin the process of priming, leave the device and then periodically check to see that priming has occurred without any exposure of the fluid to the environment.

While the membrane 24, described with reference to the embodiments of FIGS. 2A-8B to be part of the luer cap 20, it will be understood that the membrane 24 may instead, or in addition, be provided in alternate locations within the infusion system, such as along the male luer 8 received in the luer cap, along an administration tube 4 upstream of a luer 8, or as part of the spiked port or similar docking interface of a medical bag or other fluid source used to supply fluid to the infusion system.

Figure 9A:
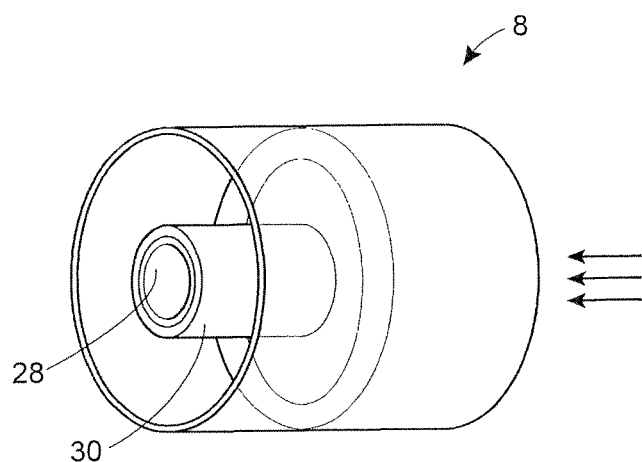
FIG. 9A is an enlarged perspective view of an alternate embodiment of the present disclosure, illustrating a luer of a medical fluid administration or infusion set, prior to a point at which the medical fluid administration or infusion set is primed, wherein a male projection of the luer is comprised of an opaque membrane (when dry) or of a membrane exhibiting a first visible characteristic when dry and a second visible characteristic when wet.
Figure 9B:
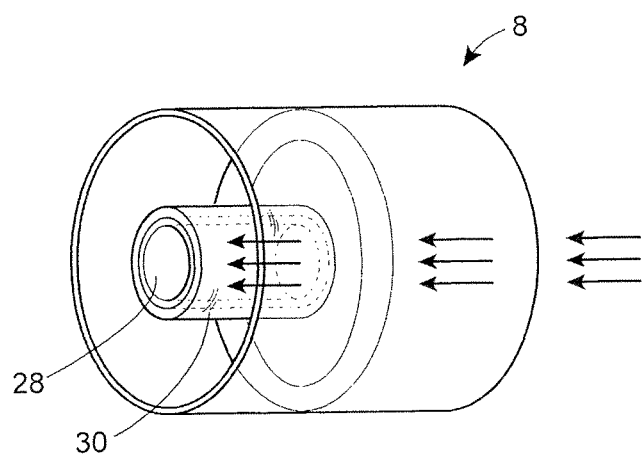
FIG. 9B is an enlarged perspective view of the luer of FIG. 9A, wherein the male projection of the luer has changed from opaque to transparent, or has changed from the first visible characteristic to the second characteristic, to provide an indication that the medical fluid administration or infusion set is fully primed.

Turning to FIGS. 9A and 9B, an alternate embodiment of the present disclosure is illustrated in the form of a luer 8 provided with a fluid-permeable tubular member 28 within a tubular casing 30. The directional arrows in FIG. 9A are intended to illustrate fluid flow that has not yet reached the luer 8 (i.e., prior to priming), and the directional arrows in FIG. 9B are intended to illustrate fluid flow through the interior of the luer 8 (i.e., when the luer is in its primed state). The tubular casing 30 is formed of a material similar to the membrane 24, that exhibits a first visible characteristic (such as being opaque) when dry, as illustrated in FIG. 9A, and exhibits a second visible characteristic (such as becoming less opaque) when wet, as illustrated in FIG. 9B. As the luer 8 becomes primed and ready to introduce fluid to the patient, the fluid-permeable tubular member 28 permits some of the fluid flowing therein to reach and activate the material of the tubular casing 30 in order to transform the tubular casing 30 from exhibiting the first visible characteristic to exhibiting the second visible characteristic (e.g., to change from opaque to less-opaque). To further enhance the visibility and facilitate discerning the opaque state of the tubular casing 30 from the less-opaque state, the fluid-permeable tubular member 28 may be colored or may be provided with some other indicia thereon, such color or other indicia only becoming visible through the tubular casing 30 upon the tubular casing 30 becoming wet. Appearance of the color or other indicia of the fluid-permeable tubular member 28 through the tubular casing 30 thereby provides an indication that the luer 8 is primed.

Figure 10A:
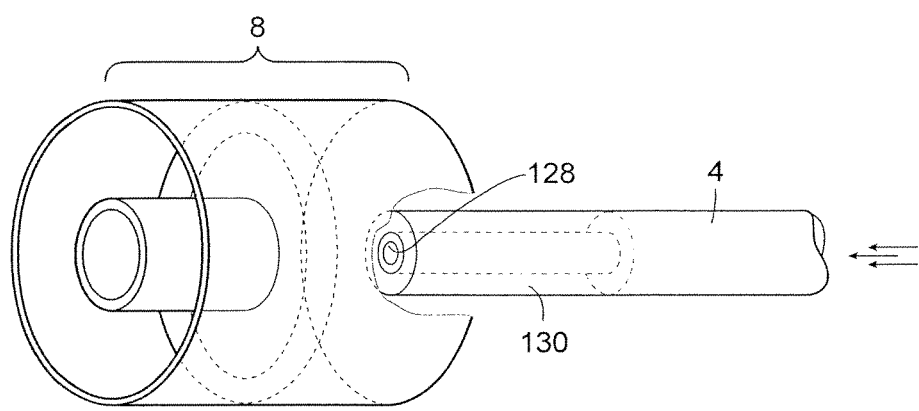
FIG. 10A is an enlarged perspective view of an alternate embodiment of the present disclosure, illustrating a luer and tubing leading thereto, wherein at least a portion of the tubing upstream of the luer is comprised of an opaque membrane (when dry) or of a membrane exhibiting a first visible characteristic when dry and a second visible characteristic when wet, with the membrane in its opaque condition, i.e. exhibiting the first visible characteristic, to reflect its un-primed condition.
Figure 10B:
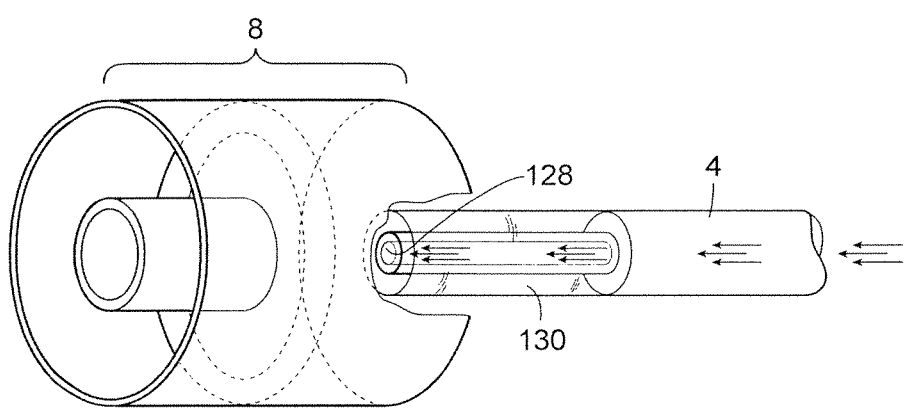
FIG. 10B is an enlarged perspective view of the luer and tubing of FIG. 10A, wherein the portion of the tubing upstream of the luer comprised of the membrane has changed from opaque to less opaque, or has changed from the first visible characteristic to the second characteristic, to provide an indication that the medical fluid administration or infusion set is fully primed, or at least almost fully primed.

In FIGS. 10A and 10B, the membrane exhibiting different visible characteristics when wet is located along an administration tube 4 upstream of a luer 8. At least a portion of the administration tube 4, preferably including a region of the administration tube 8 immediately upstream of the luer 8, is provided with a fluid-permeable tubular member 128 within a tubular casing 130. The directional arrows in FIG. 10A are intended to illustrate fluid flow through the administration tube 4, but that has yet to reach the portion of the administration tube 4 provided with the fluid-permeable tubular member 128 and tubular casing 130.

As in the embodiment illustrated in FIGS. 9A and 9B, the tubular casing 130 is formed of a material that exhibits a first visible characteristic (such as being opaque) when dry, as illustrated in FIG. 10A, and exhibits a second visible characteristic (such as becoming less opaque) when wet, as illustrated in FIG. 10B. In this embodiment, once the tubular casing 130 of the portion of the administration tube 4 upstream of the luer 8 changes from the first visible characteristic to the second visible characteristic, it will be understood that the fluid has reached that point of the tubing. Like in the previous embodiment, the fluid-permeable tubular member 128 permits some of the fluid flowing therein to reach and activate the material of the tubular casing 130. Also, the fluid-permeable tubular material 128 may be colored or may be provided with some other indicia thereon, in order to enhance the visibility of a change in state of the tubular casing 130 from exhibiting the first visible characteristic to exhibiting the second visible characteristic.

Figure 11A:
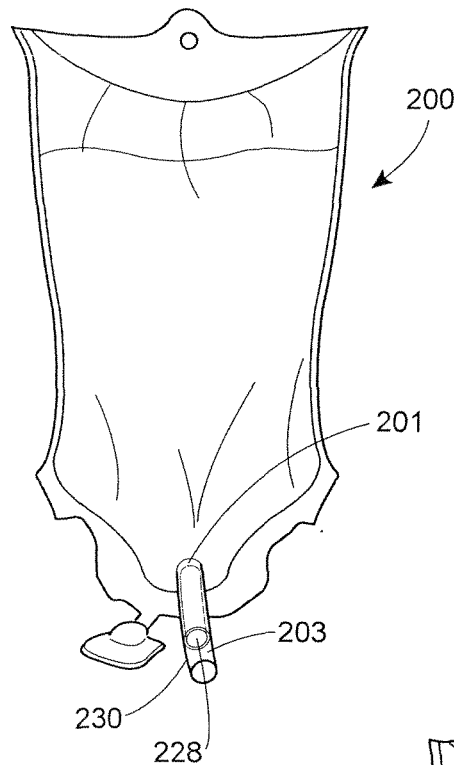
FIG. 11A is a side view of a medical bag having a port made of a membrane that becomes opaque when dry but is initially less-opaque when wet, or that exhibits a first visible characteristic when wet and a second visible characteristic when dry, to reflect that there is still fluid flowing from the associated medical bag, with the membrane of the port in its less-opaque condition or exhibiting the first visible characteristic, to reflect the presence of fluid flowing from the medical bag.
Figure 11B:
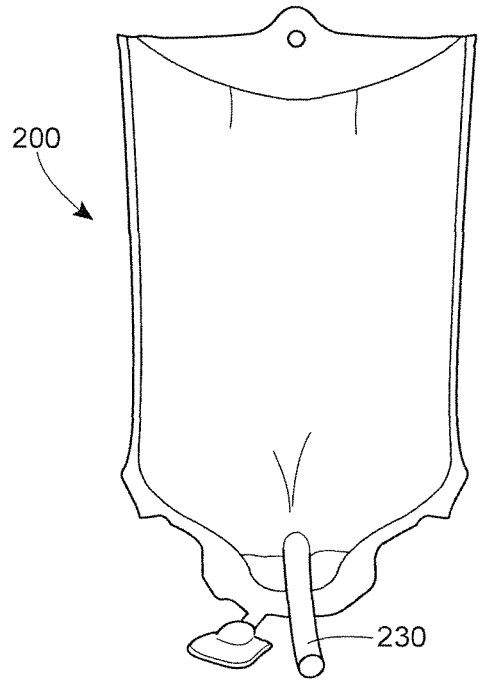
FIG. 11B is a side view of the medical bag of FIG. 11A, wherein the membrane of the port has changed from less-opaque, or the first visible characteristic, to opaque, or the second visible characteristic, to reflect an absence of fluid flowing from the medical bag.

In yet another alternate embodiment, illustrated in FIGS. 11A and 11B, a medical bag 200 or similar fluid source used to supply fluid to the infusion system may be provided with a port 201 having a connecting tube 203. One of the port 201 or connecting tube 203 includes a fluid-permeable tubular member 228 surrounded by an indicator 230. In this embodiment, since the indicator is provided at an upstream end of the infusion system, a change in visible characteristics of the indicator from a first visible characteristic, associated with fluid within the connecting tube 203, and a second characteristic, associated with an absence of fluid flow within the connecting tube 203, serves as an indication that the medical bag 200 is empty or nearly empty. In an alternate embodiment, the indicator 230 may line the passageway formed by a segment of one of the port tubing or connecting tube.

Figure 12:
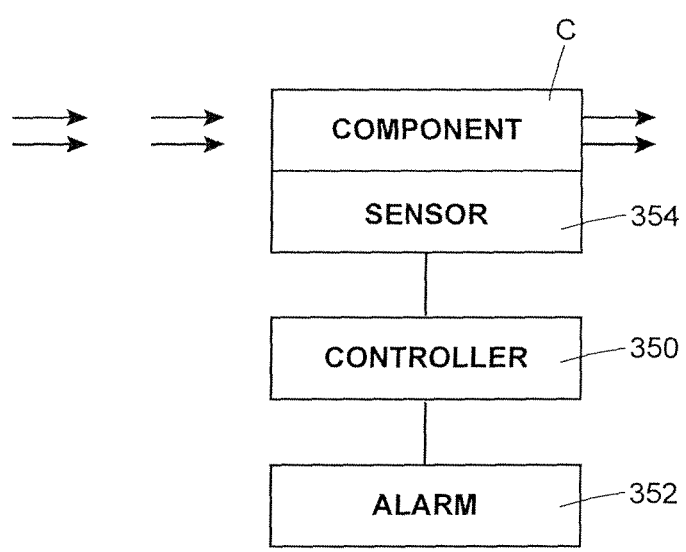
FIG. 12 is a schematic diagram illustrating a sensing system of the present disclosure that that communicates a signal to a controller in operable communication with a device that emits at least one of an audible or a visual alarm that alerts a medical professional to a change in status of flow through a given component of a medical fluid administration or infusion set.

FIG. 12 illustrates an additional or alternate means for detection of the presence, or absence, of fluid flow through a given component C of an infusion system. This includes a sensing system 300 that will communicate a signal to a controller 350 in operable communication with an alarm device 352. The alarm device 352 emits at least one of an audible or a visual alarm that alerts a medical professional to a change in status of flow through the given component. The alarm may take several forms, with the following examples meant to be illustrative as opposed to limiting: A pre-recorded audible message, a text message, an e-mail, or a vibration of a pager device worn by the medical professional. The alarm may be distinct for different individual patients, enabling one or more medical professionals to whom the alarm is directed to distinguish, by virtue of the characteristics of the alarm, which of a plurality of patient's infusion system is fully primed.

The directional arrows in FIG. 12 are intended to represent the flow of fluid through a particular component having a flow indicator of an infusion system. A sensor 354 is provided that detects the change in opaqueness or degree of transparency. The sensor 354 maybe a light sensor, so as to be activated when the indicator becomes transparent upon the presence (or absence) of fluid flow through the associated infusion system indicator. For example, the indicator may be in the form of a membrane as described above which lines the passageway formed by a segment of the tubing. That segment will be opaque and block the transmission of light. The sensor 354 may be spaced from an interior fluid path and indicator for example by sensing for a light signal which is being blocked from being transmitted through the tubing due to the opaqueness of the priming indicator. Upon fluid flowing through the segment and contacting the indicator, the indicator becomes more transparent, thereby allowing at last some portion of the light signal to reach the sensor 354 to activate the sensor. Upon activation, the sensor 354 communicates a signal to the controller 350, which in turn operates the associated alarm device 352 to generate an alarm, such as in the form of one or more of the example alarm formats identified above.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

What is claimed is:

1. A device for indicating the presence of fluid in a portion of an infusion line, comprising:
   a housing positioned along the infusion line and having a hollow interior arranged for receiving a flow of the fluid when in use;
   a member located within said housing interior, having an exterior surface and being inaccessible to a user of the housing when the housing is in use;
   a microporous membrane that exhibits a first visual characteristic when dry and that exhibits a second visual characteristic when wet with the fluid, the microporous membrane being positioned within said interior of said housing and inaccessible to a user when the housing is in use, said microporous membrane covering at least a portion of said exterior surface; and
   wherein said exterior surface includes indicia that, upon said microporous membrane becoming wet with the fluid flowing into said hollow housing interior, becomes visible from an exterior of said housing through both said microporous membrane and said housing as the fluid flows from a first end of said housing to a second end.

2. The device of claim 1, wherein the microporous membrane comprises strands that change from an opaque condition to a less-opaque condition when exposed to fluid having a refractive index that matches or substantially matches the refractive index of the strands.

3. The device of claim 1, wherein the member is a rod provided within an end of said housing that is connected to an end of a tube.

4. The device of claim 3, further comprising a hydrophobic vent to allow air to flow out of said housing while preventing fluid from flowing therethrough.

5. The device of claim 4 wherein one end of said member is adjacent said hydrophobic vent.

6. The device of claim 1, wherein said microporous membrane is provided on a tubular casing provided on at least one component of an infusion set and the surface is a fluid-permeable tubular member.

7. The device of claim 6, wherein said surface is provided in a connecting tube of a port of a fluid-containing bag of said infusion set.

8. The device of claim 1, wherein the indicia on the surface includes at least one of a group including a color that is distinct from a color of said microporous membrane when dry, text, and an image.

9. The device of claim 1, wherein said housing is a luer cap defining a cavity, and wherein said surface is provided on a rod inserted into said cavity.

10. The device of claim 9, wherein said rod has a cross-sectional shape that is one of circular, rectangular, and hexagonal.

11. The device of claim 1, wherein said member extends axially within said housing and said microporous membrane on said housing becomes visible as the fluid fills said housing.

12. A device for indicating the presence of fluid in a portion of an infusion line, comprising:
- a housing positioned along the infusion line and having a hollow interior arranged for receiving a flow of fluid inaccessible to a user when the infusion line is in use;
- a hydrophobic vent located in said housing and configured for allowing air to flow out of said housing while preventing fluid from flowing therethrough;
- a member having an exterior surface and being positioned within the interior of said housing;
- a microporous membrane that exhibits a first visual characteristic when dry and that exhibits a second visual characteristic when wet with the fluid, said microporous membrane covering at least a portion of said exterior surface of said member; and
- wherein said exterior surface includes indicia that, upon said microporous membrane becoming wet with the fluid flowing into said hollow interior of said housing, becomes visible from an exterior of said housing through both said microporous membrane and said housing, said housing being made of a material through which a change in appearance of said microporous membrane is visible.

13. The device of claim 12, wherein said housing is a luer cap.

14. The device of claim 12, wherein one end of said member is adjacent said hydrophobic vent.

15. The device of claim 12, wherein said housing is an administration tube in an infusion system.

16. The device of claim 12, wherein said housing is a port of a medical bag in an infusion system.

17. The device of claim 12, wherein said housing is a connecting tube in an infusion system.

* * * * *